United States Patent [19]
Franz et al.

[11] Patent Number: 5,952,265
[45] Date of Patent: Sep. 14, 1999

[54] SYNERGISTIC HERBICIDAL COMBINATION

[75] Inventors: Richard Lynn Franz, Richmond; John Hawtree, Surrey; Khosro Khodayari, Walnutcreek, all of Calif.

[73] Assignee: Zeneca Limited, London, United Kingdom

[21] Appl. No.: 09/145,162

[22] Filed: Sep. 2, 1998

Related U.S. Application Data

[60] Provisional application No. 60/090,102, Sep. 3, 1997.

[51] Int. Cl.$^6$ .............................. A01N 37/18; A01N 43/00
[52] U.S. Cl. ............................................. 504/129; 504/149
[58] Field of Search ...................................... 504/129, 149

[56] References Cited

FOREIGN PATENT DOCUMENTS

| 0190724 | 8/1986 | European Pat. Off. . |
|---|---|---|
| 5 2096-737 | 2/1976 | Japan . |
| 5 4059-328 | 10/1977 | Japan . |
| 5 4059-334 | 10/1977 | Japan . |
| 5 9016-807 | 7/1982 | Japan . |

*Primary Examiner*—Allen J. Robinson

[57] ABSTRACT

Control of weeds in a rice crop is obtained by applying to the crop, the weeds, or the locus of either or both, a herbicidal composition containing molinate and acetochlor in a weight ratio of from about 250:1.5 to about 5:1.

14 Claims, No Drawings

5,952,265

SYNERGISTIC HERBICIDAL COMBINATION

This application claims the benefit of U.S. Provisional Application No. 60/090,102, filed Sep. 9, 1997.

BACKGROUND AND PRIOR ART

This invention pertains to synergistic herbicidal combinations, particularly such combinations for use in controlling weeds in a rice crop.

Molinate (S-ethyl hexahydro-1H-azepine-1-carbothioate) is a thiocarbamate herbicide which has been used to control weeds in rice crops for a number of years, and is generally sold under products bearing the trademark ORDRAM®. In different formulations and strengths, molinate is applied pre-plant, pre-flood or post-flood to control a wide range of weeds in rice crops, and is generally applied at rates ranging from about 500 to about 11,000 g/ha. However, as with many pesticides, it would be desirable to be able to achieve weed control while using a lower application rate of molinate. This could also result in less impact upon the environment and/or upon workers handling the product.

It has now been found that, surprisingly, combining of a lesser amount of the herbicide acetochlor with molinate can produce a synergistic effect such that equivalent weed control can be obtained with a lesser amount and/or application rate of molinate.

Acetochlor, or 2-chloro-2'-methyl-6'-ethyl-N (ethoxymethyl)acetanilide is an acetamide or haloacetanilide herbicide which is sold under several trademarks, notably SURPASS® and HARNESS®, and in microencapsulated formulations under trademarks such as TOPNOTCH™ AND FULTIME™. This herbicide is sold primarily for use in corn crops, and also is known to be useful for certain other crops such as soybeans. However, acetochlor is generally considered to be too injurious to rice to be used as the primary herbicide for controlling weeds in rice crops. In accordance with the present invention, however, the use of acetochlor in an amount which produces substantially no phytotoxicity to a rice crop, in combination with molinate, particularly a lesser amount or lower application rate than is normally used, produces a synergistic effect, resulting in good control of weeds in rice crops in either pre-flood or post-flood applications.

SUMMARY OF THE INVENTION

This invention comprises a herbicidal composition as well as a method of controlling weeds in rice crops.

In one aspect, this invention relates to a synergistic herbicidal composition comprising molinate and acetochlor.

In a second aspect, it comprises a herbicidal composition comprising molinate and acetochlor in a weight ratio of from about 250:1.5 to about 5:1, respectively.

In another aspect, this invention comprises a method of controlling weeds in a rice crop comprising applying to said crop, said weeds or the locus of either or both, a synergistic combination comprising molinate and acetochlor, particularly in a weight ratio of from about 250:1.5 to about 5:1, respectively.

DETAILED DESCRIPTION OF THE INVENTION

The invention involves the use of the combination of the herbicides molinate and acetochlor to control weeds in a rice crop. The combination, within the scope of this invention, demonstrates synergistic effects, that is, effects that would have been unexpected from the performance of the two herbicides individually against the same weeds under similar circumstances.

According to the invention, weeds are controlled in the presence of a rice crop by treating the crop, the weeds, or the locus of either or both, with a herbicidally effective amount of a synergistic combination of the herbicides molinate and acetochlor. In general, we have found that synergy is demonstrated when the combination includes these two herbicides in a weight ratio respectively, of from about 250:1.5 to about 5:1, preferably, from about 250:3.25 to about 12:1, most preferably from about 36:1 to about 12:1. However, our discovery is that of synergism between molinate and acetochlor, and is not necessarily limited to combinations of these herbicides within these weight ratios, as synergy may exist at others.

This combination produces synergistic or unexpected control of weeds in rice when applied at various times, and to rice planted in different ways. To control the weeds, the combination may be applied prior to planting, after planting but prior to flooding (pre-flood, post-emergence) or after emergence of the rice and flooding (post-flood, post-emergence) and may be applied to either direct seeded or transplanted rice.

To be used in combination, it is not necessary that the two herbicides molinate and acetochlor, be applied in a physically combined form, or even at the same time. The combination effect results so long as the two herbicides are present at the same time in the rice crop, regardless of when they were applied. Thus, for instance, a physical combination of the two herbicides could be applied, or one could be applied earlier than the other. For instance, one of the two herbicides could be applied even prior to planting the rice in a controlled release formulation such as a microencapsulated formulation, and the other applied subsequently in a conventional liquid or solid formulation, so long as the earlier-applied herbicide is still present in the soil when the second is applied, and so long as the weight ratio of available herbicides falls within that disclosed and claimed herein.

Either herbicide could thus be applied in liquid or solid form, or a combination product containing both herbicides could be produced, again, in either liquid or solid form. Typical liquid formulations include emulsions, suspensions (including suspensions containing microcapsules), solutions, emulsifiable concentrates, and flowables. Solid products include forms such as granules, wettable powders, water-dispersible solid products (including water-dispersible granules containing microencapsulated pesticides) or dusts. Both types of compositions will generally contain, in addition to the active herbicide, other ingredients such as solvents, wetting agents, suspending agents, anti-caking agents, dispersing agents, emulsifiers, antifreeze agents, antifoam agents, and other additives.

Either herbicide, or both, may be utilized in one of a number of known forms of controlled release compositions. Such compositions provide relatively slow or controlled release of the active ingredient into the environment and include, for example, encapsulations, microencapsulations, and various forms of controlled release granules.

Combination products or compositions according to this invention, may contain the two herbicides in numerous different physical forms. In some cases, a combination product may be produced by simply physically mixing ("tank-mixing") commercially available products containing the active herbicides, for example, two emulsifiable concentrates containing the herbicides, so long as all the ingredients of the two products are relatively compatible. Alternatively, a package may be manufactured and sold which contains overall the two herbicides in separate containers, but packaged together, commonly termed a "twin-pack". A twin-pack is particularly suitable for the herbicidal compositions herein, since the amount of molinate is substantially greater than that of acetochlor, so that an overall product package can be produced containing a relatively large container of a molinate-containing herbicide product together with a relatively small container of an acetochlor-containing herbicidal product.

Alternatively, previously prepared compositions ("premixes") containing the two herbicides can be produced. Since both acetochlor and molinate are liquids under normal conditions, liquid compositions would tend to be preferred. Typical liquid compositions would include an emulsifiable concentrate containing both herbicides, and a two-phase emulsion (or microemulsion) with one herbicide in each phase. One typical type of premixed liquid formulation containing the two herbicides would be an emulsifiable concentrate and would contain, for example, 900 g/l molinate and either 25 or 37.5 g/l acetochlor, using kerosene as the solvent and including, as emulsifiers, 1.50 weight percent Sponto 217 and 3.50 weight percent Sponto 221ER. The Sponto products are emulsifiers comprising blends of ethoxylated nonylphenyl alcohols and calcium dodecylbenzene sulfonates.

However, in practice, both herbicides are currently also sold as solid formulations, that is, impregnated granules, so that a similar solid product containing both herbicides could likewise be produced, as impregnated granules. Similarly, other solid formulations such as wettable powders or dusts could be prepared.

Again similarly, using appropriate ingredients and conditions, it would be possible to prepare microencapsulated products in which one or both herbicides are contained within a microcapsule and said microencapsulated products could be sold in either liquid form (i.e., capsule suspensions) or solid form (i.e., water-dispersible granules produced by drying of microcapsule suspensions). One type of liquid form would be a microcapsule suspension in which one of the herbicides is contained within the capsules while the other is present in a nonencapsulated form, in the continuous liquid phase. Another type would be a suspension containing molinate and acetochlor separately encapsulated. The types of formulations or compositions which may contain these two herbicides is not limited by those enumerated herein, as other types of formulations would likely be envisaged by those skilled in the art.

The control of weeds by the combination of acetochlor and molinate is illustrated by the following examples:

EXAMPLE 1

This example simulates application of the combination of molinate and acetochlor in a direct seeded rice culture under conditions typical of the Americas. Combinations of molinate and acetochlor in the indicated amounts were applied in the greenhouse at the application rates shown in Table 1 (in terms of grams per hectare of the herbicide or herbicides) to flats containing rice (*Oryza sativa,* variety Katy) and the weeds barnyardgrass (*Echinochloa crusgalli,* ECHCG) and smallflower flatsedge (*Cyperus difformis,* CYPDI) at the pre-flood postemergence stage, and at the 2-leaf growth stage of the barnyardgrass. The weeds had been grown separately to the 2-leaf stage, then transplanted to the rice flats. Results of these tests are shown in Table 1, below, in terms of percent control or injury as compared to an untreated check flat. A rating of 100% indicates complete control; of 0% indicates no effect.

TABLE 1

| Compound(s) | Rate of molinate (g/ha) | Rate of acetochlor (g/ha) | Rice injury % (7 days) | Rice injury % (27 days) | ECHCG (% control) | CYPDI (% control) |
|---|---|---|---|---|---|---|
| molinate | 250 | | 0 | 0 | 66 | 0 |
| molinate/acetochlor | 250 | 6 | 1 | 0 | 93 | 8 |
| molinate/acetochlor | 250 | 13 | 5 | 0 | 100 | 13 |
| molinate/acetochlor | 250 | 25 | 36 | 0 | 100 | 73 |
| molinate/acetochlor | 250 | 50 | 59 | 0 | 100 | 100 |
| molinate/acetochlor | 250 | 100 | 44 | 4 | 100 | 100 |
| molinate | 500 | | 0 | 0 | 80 | 3 |
| molinate/acetochlor | 500 | 6 | 4 | 0 | 88 | 8 |
| molinate/acetochlor | 500 | 13 | 29 | 1 | 100 | 36 |
| molinate/acetochlor | 500 | 25 | 53 | 1 | 100 | 100 |
| molinate/acetochlor | 500 | 50 | 54 | 4 | 100 | 100 |
| molinate/acetochlor | 500 | 100 | 55 | 3 | 100 | 100 |
| molinate | 1000 | | 0 | 0 | 80 | 3 |
| molinate/acetochlor | 1000 | 6 | 6 | 0 | 96 | 44 |
| molinate/acetochlor | 1000 | 13 | 53 | 3 | 100 | 81 |
| molinate/acetochlor | 1000 | 25 | 44 | 0 | 100 | 100 |
| molinate/acetochlor | 1000 | 50 | 55 | 10 | 100 | 100 |
| molinate/acetochlor | 1000 | 100 | 63 | 8 | 100 | 100 |
| molinate | 2000 | | 6 | 1 | 90 | 69 |
| molinate/acetochlor | 2000 | 6 | 9 | 0 | 100 | 79 |
| molinate/acetochlor | 2000 | 13 | 45 | 0 | 99 | 100 |
| molinate/acetochlor | 2000 | 25 | 44 | 4 | 100 | 100 |
| molinate/acetochlor | 2000 | 50 | 61 | 6 | 100 | 100 |

TABLE 1-continued

| Compound(s) | Rate of molinate (g/ha) | Rate of acetochlor (g/ha) | Rice injury % (7 days) | Rice injury % (27 days) | ECHCG (% control) | CYPDI (% control) |
|---|---|---|---|---|---|---|
| molinate/acetochlor | 2000 | 100 | 60 | 4 | 100 | 100 |
| acetochlor tech | | 6 | 1 | 0 | 93 | 0 |
| | | 13 | 5 | 0 | 99 | 6 |
| | | 25 | 21 | 0 | 99 | 24 |
| | | 50 | 50 | 0 | 100 | 100 |
| | | 100 | 48 | 0 | 100 | 100 |

EXAMPLE 2

This example demonstrates preflood postemergence application of molinate and acetochlor to a direct seeded rice culture under auditors typically Southeast Asia. Dry rice seed (Kaybonnet variety) is soaked for 24 hours or more. The soil is puddled to the right consistency and partially drained. The pre-germinated seeds are then broadcast to the surface of the soil and are grown to the 3 leaf stage. Weeds are grown separately to the 2 leaf growth stage and added to the tubs. Herbicide application is by spraying or broadcasting of chemical. Tubs are flooded 1 week or more after application. The results of these are shown in the following Table 2.

TABLE 2

| Compound(s) | Rate of molinate (g/ha) | Rate of acetochlor (g/ha) | Rice injury % (7 days) | Rice injury % (28 days) | ECHCG (% control) | CYPDI (% control) |
|---|---|---|---|---|---|---|
| molinate | 250 | | 1 | 0 | 0 | 0 |
| molinate/acetochlor | 250 | 6 | 1 | 0 | 0 | 54 |
| molinate/acetochlor | 250 | 13 | 11 | 1 | 30 | 61 |
| molinate/acetochlor | 250 | 25 | 15 | 3 | 54 | 85 |
| molinate/acetochlor | 250 | 50 | 54 | 6 | 100 | 96 |
| molinate/acetochlor | 250 | 100 | 69 | 15 | 100 | 95 |
| molinate | 500 | | 3 | 0 | 0 | 8 |
| molinate/acetochlor | 500 | 6 | 0 | 1 | 8 | 33 |
| molinate/acetochlor | 500 | 13 | 6 | 3 | 54 | 73 |
| molinate/acetochlor | 500 | 25 | 29 | 0 | 100 | 89 |
| molinate/acetochlor | 500 | 50 | 58 | 3 | 100 | 90 |
| molinate/acetochlor | 500 | 100 | 65 | 25 | 100 | 99 |
| molinate | 1000 | | 0 | 0 | 8 | 25 |
| molinate/acetochlor | 1000 | 6 | 1 | 0 | 63 | 71 |
| molinate/acetochlor | 1000 | 13 | 3 | 3 | 92 | 79 |
| molinate/acetochlor | 1000 | 25 | 50 | 1 | 100 | 96 |
| molinate/acetochlor | 1000 | 50 | 56 | 6 | 100 | 93 |
| molinate/acetochlor | 1000 | 100 | 65 | 39 | 100 | 95 |
| molinate | 2000 | | 11 | 0 | 90 | 58 |
| molinate/acetochlor | 2000 | 6 | 6 | 3 | 100 | 73 |
| molinate/acetochlor | 2000 | 13 | 5 | 1 | 100 | 86 |
| molinate/acetochlor | 2000 | 25 | 46 | 3 | 100 | 95 |
| molinate/acetochlor | 2000 | 50 | 59 | 4 | 100 | 96 |
| molinate/acetochlor | 2000 | 100 | 59 | 13 | 100 | 99 |
| acetochlor tech | | 6 | 5 | 0 | 0 | 24 |
| | | 13 | 3 | 3 | 28 | 73 |
| | | 25 | 14 | 6 | 38 | 65 |
| | | 50 | 39 | 4 | 65 | 91 |
| | | 100 | 64 | 10 | 79 | 91 |

EXAMPLE 3

This example involved tests conducted using postflood, postemergence application (at the 2-leaf stage of barnyardgrass) in transplanted rice variety *Kushiki kari*). Rice is grown to the 2–4 leaf stage away separately from the trial tubs. The soil in the tub is puddled until a blend is achieved. The rice plants are then transplanted into this blend. Weeds (2 leaf stage) are either grown separately and transplanted in or are grown in the tub on the blended soil. Herbicide application typically takes place by injection or broadcasting of chemical after flooding. The results are shown in the following Table 3.

TABLE 3

| Compound(s) | Rate of molinate (g/ha) | Rate of acetochlor (g/ha) | Rice injury % (7 days) | Rice injury % (28 days) | ECHCG (% control) | CYPDI (% control) |
| --- | --- | --- | --- | --- | --- | --- |
| molinate | 250 | | 0 | 0 | 63 | 20 |
| molinate/acetochlor | 250 | 6 | 0 | 0 | 100 | 85 |
| molinate/acetochlor | 250 | 13 | 0 | 5 | 100 | 90 |
| molinate/acetochlor | 250 | 25 | 0 | 0 | 100 | 100 |
| molinate/acetochlor | 250 | 50 | 43 | 33 | 100 | 100 |
| molinate/acetochlor | 250 | 100 | 45 | 35 | 100 | 95 |
| molinate | 500 | | 0 | 0 | 88 | 25 |
| molinate/acetochlor | 500 | 6 | 0 | 3 | 100 | 90 |
| molinate/acetochlor | 500 | 13 | 3 | 0 | 99 | 100 |
| molinate/acetochlor | 500 | 25 | 5 | 0 | 100 | 90 |
| molinate/acetochlor | 500 | 50 | 43 | 15 | 100 | 95 |
| molinate/acetochlor | 500 | 100 | 58 | 45 | 100 | 100 |
| molinate | 1000 | | 0 | 0 | 98 | 43 |
| molinate/acetochlor | 1000 | 6 | 8 | 8 | 100 | 100 |
| molinate/acetochlor | 1000 | 13 | 8 | 18 | 100 | 93 |
| molinate/acetochlor | 1000 | 25 | 10 | 3 | 100 | 100 |
| molinate/acetochlor | 1000 | 50 | 35 | 30 | 100 | 95 |
| molinate/acetochlor | 1000 | 100 | 68 | 73 | 100 | 100 |
| molinate | 2000 | | 0 | 0 | 99 | 75 |
| molinate/acetochlor | 2000 | 6 | 0 | 0 | 100 | 90 |
| molinate/acetochlor | 2000 | 13 | 5 | 10 | 100 | 95 |
| molinate/acetochlor | 2000 | 25 | 5 | 3 | 100 | 93 |
| molinate/acetochlor | 2000 | 50 | 40 | 25 | 100 | 100 |
| molinate/acetochlor | 2000 | 100 | 65 | 78 | 100 | 100 |
| acetochlor | | 6 | 5 | 15 | 45 | 73 |
| | | 13 | 3 | 13 | 90 | 78 |
| | | 25 | 13 | 33 | 100 | 88 |
| | | 50 | 45 | 43 | 100 | 100 |
| | | 100 | 60 | 58 | 100 | 100 |

From the foregoing examples, the following can be noted:

1. In these tests, molinate applied alone at a rate of 2,000 g/ha provided sufficiently good control of weeds such that further control when acetochlor was added, even in small amounts, appears to have been no more than additive.
2. In some tests, combinations of molinate and acetochlor within the ranges described herein did not show synergy, and this is not unexpected, as synergy is normally not shown for all possible combinations of herbicides within a given range, or on all weeds.
3. In some cases, combinations within this range showed early injury to rice (at 7 days after application) but subsequently (at 27–28 days after application), the injury was no longer apparent or had lessened markedly. Such injury to rice is acceptable if the rice recovers within 3–4 weeks.

We claim:

1. A herbicidal composition comprising synergistic herbicidally effective amounts of molinate and acetochlor in a weight ratio of from about 250:1.5 to about 5:1.

2. A herbicidal composition according to claim 1 in which the weight ratio is from about 250:3.25 to about 12:1.

3. A herbicidal composition according to claim 1 in which the weight ratio is from about 36:1 to about 12:1.

4. A liquid herbicidal composition according to claim 1.

5. A solid herbicidal composition according to claim 1.

6. A controlled release herbicidal composition according to claim 1.

7. A herbicidal composition according to claim 6 in which at least one of molinate and acetochlor is contained in microcapsules.

8. A method of controlling weeds in the presence of a rice crop comprising applying to said crop, said weeds, or the locus of said crop and/or said weeds, a herbicidally-effective amount of a composition according to claim 1.

9. A method of controlling weeds in the presence of a rice crop comprising applying to said crop, said weeds, or the locus of said crop and/or said weeds, a herbicidally-effective amount of a composition according to claim 2.

10. A method of controlling weeds in the presence of a rice crop comprising applying to said crop, said weeds, or the locus of said crop and/or said weeds, a herbicidally-effective amount of a composition according to claim 3.

11. A method of controlling weeds in the presence of a rice crop comprising applying to said crop, said weeds, or the locus of said crop and/or said weeds, a herbicidally-effective amount of a composition according to claim 4.

12. A method of controlling weeds in the presence of a rice crop comprising applying to said crop, said weeds, or the locus of said crop and/or said weeds, a herbicidally-effective amount of a composition according to claim 5.

13. A method of controlling weeds in the presence of a rice crop comprising applying to said crop, said weeds, or the locus of said crop and/or said weeds, a herbicidally-effective amount of a composition according to claim 6.

14. A method of controlling weeds in the presence of a rice crop comprising applying to said crop, said weeds, or the locus of said crop and/or said weeds, a herbicidally-effective amount of a composition according to claim 7.

* * * * *